United States Patent [19]

Hutson, Jr.

[11] Patent Number: 4,500,490
[45] Date of Patent: Feb. 19, 1985

[54] CATALYTIC ALKYLATION OF HYDROCARBONS

[75] Inventor: Thomas Hutson, Jr., Bartlesville, Okla.

[73] Assignee: Phillips Petroleum Company, Bartlesville, Okla.

[21] Appl. No.: 296,090

[22] Filed: Aug. 26, 1981

Related U.S. Application Data

[62] Division of Ser. No. 027,322, Apr. 5, 1979, Pat. No. 4,304,947.

[51] Int. Cl.³ .................... G01N 33/00; G01N 14/00
[52] U.S. Cl. .................................... 422/62; 422/111; 422/132; 422/189; 422/235; 422/109
[58] Field of Search .............. 422/62, 111, 132, 140, 422/141, 144, 147, 234, 235, 188, 189; 585/301, 303, 304

[56] References Cited

U.S. PATENT DOCUMENTS

| | | | |
|---|---|---|---|
| 2,407,873 | 4/1946 | Evering et al. | 585/301 |
| 2,476,750 | 7/1949 | Matuszak | 585/719 |
| 3,787,518 | 1/1974 | Anderson | 585/716 |
| 3,864,346 | 2/1975 | Child et al. | 422/111 |
| 3,867,473 | 2/1975 | Anderson | 585/719 |
| 4,046,516 | 9/1977 | Burton et al. | 585/716 |
| 4,061,471 | 12/1977 | Sze | 422/189 |
| 4,161,497 | 7/1979 | Makovec et al. | 585/716 |
| 4,214,115 | 7/1980 | Makovec et al. | 585/716 |

Primary Examiner—Michael S. Marcus

[57] ABSTRACT

An integrated process for the simultaneous alkylation of at least one isoparaffinic hydrocarbon with at least one $C_4$ olefinic hydrocarbon and at least one isoparaffinic hydrocarbon with at least one olefinic hydrocarbon selected from the group consisting of $C_3$, $C_5$ and higher olefinic hydrocarbons and mixtures thereof, comprising: contacting a first alkylatable hydrocarbon comprising an isoparaffinic hydrocarbon with a first alkylating agent comprising at least one olefinic hydrocarbon selected from the group consisting of $C_3$, $C_5$ and higher olefinic hydrocarbons and mixtures thereof in the presence of an acid-type catalyst, to alkylate said first alkylatable hydrocarbon; separating the effluent from the first alkylation reaction into a first alkylate phase and a first catalyst phase containing catalyst-soluble oil; recycling at least a portion of said first catalyst phase to said first alkylation reaction; contacting a second alkylatable hydrocarbon comprising an isoparaffinic hydrocarbon with a second alkylating agent comprising at least one $C_4$ olefinic hydrocarbon in the presence of an acid-type catalyst, to alkylate said second alkylatable hydrocarbon; separating the effluent from the second alkylation reaction into a second alkylate phase and a second catalyst phase containing catalyst-soluble oil; recycling at least a portion of said second catalyst phase to said second alkylation reaction; and adding at least a portion of one of said first catalyst phase, said second catalyst phase or both of said first and said second catalyst phases to the other of said first catalyst phase and said second catalyst phase.

17 Claims, 7 Drawing Figures

CATALYTIC ALKYLATION OF HYDROCARBONS

CROSS REFERENCE TO RELATED APPLICATIONS

The present application is a divisional application of application Ser. No. 027,322, entitled, CATALYTIC ALKYLATION OF HYDROCARBONS, filed Apr. 5, 1979 by the present inventor, now U.S. Pat. No. 4,304,947.

BACKGROUND OF THE INVENTION

The present invention relates to a catalytic alkylation process and apparatus. In a more specific aspect, the present invention relates to a catalytic alkylation process in which an alkylatable hydrocarbon is contacted with an alkylating agent in the presence of an acid-type catalyst and the catalyst is cylically circulated through the system. In yet another aspect, the present invention relates to a catalytic alkylation process and apparatus in which an acid-type catalyst is cylically circulated through the system to produce an alkylate product of improved octane number.

Numerous processes are known in the prior art for alkylating an alkylatable hydrocarbon with an alkylating agent in the presence of a catalyst. From a commercial standpoint, the most prevalent systems involve the cyclic circulation of an acid-type catalyst, such as hydrofluoric acid, sulfuric acid, etc. through a reaction zone, a separation zone on a cooling zone and back to the reaction zone.

One such process for the alkylation of hydrocarbons, utilizing the cyclic circulation of the catalyst, introduces the reactant hydrocarbons in a gaseous phase. In this system the gaseous hydrocarbon feed mixture is introduced at a high velocity to lower portion of the reaction zone and into a continuous catalyst phase maintained in the reaction zone. Suitable conditions of temperature and residence or contact time are provided in the reaction zone whereby the alkylatable hydrocarbon is alkylated. A stream comprising catalyst, alkylate product and unconsumed reactants passes from the upper portion of the reaction zone into a settling zone, wherein separation occurs between the alkylate product phase and the catalyst phase. The alkylate product phase is withdrawn from the settling zone for further processing, as by fractionation, and the catalyst phase is passed downwardly to a cooling zone and thence back into the reaction zone.

Another process, based on the cyclic circulation of the catalyst, which overcomes certain of the inherent deficiencies of the gas phase process and permits operation at low reaction temperatures, introduces the reactant hydrocarbons in the liquid phase. In this process, the hydrocarbon reactants are introduced into the bottom of the reaction zone through constricted passageways, thereby creating a liquid lift system, whose motive power comes from the difference in density of the flowing streams and to some extent from the kinetic energy of the inlet hydrocarbon stream, and at the same time creating small droplets of reactants having a high interfacial area which result in a desirably high reaction rate. The reactant hydrocarbons and catalyst move upwardly through an elongated, tube-type reaction zone, the effluent, including alkylate product, catalyst and unreacted hydrocarbons, is discharged from the reaction zone into a settler-surge vessel, an alkylate product phase is withdrawn for further processing and a catalyst phase is passed downwardly through a tube-type conduit to a cooler and thence back into the reaction zone.

It has generally been recognized in the art that in order to obtain an alkylate product of maximum octane number, the weight percent total acidity of the catalyst should not exceed a given amount. While the tolerable acidity of the catalyst will vary depending upon the reactant hydrocarbons and the temperature of operation, it is generally thought that the total acidity of the catalyst under any conditions should not be higher than about 90 percent, that alkylate products of highest octane number are obtained at acidities substantially lower than this and, consequently, that the weight percent total acidity of the catalyst for optimum octane number should be between about 87 percent and 67 percent. Consequently, the catalyst is in some way diluted so as to maintain the desired total acidity. Obviously, water would be the logical diluting agent to utilize. However, the presence of excessive amounts of water, in systems utilizing acid catalysts, creates problems in that, in conjunction with the acid, water is highly corrosive to the alkylation system and catalyst handling system. Therefore, the acid catalyst is normally utilized in an essentially anhydrous condition. There is a tendency in alkylation systems for water to accumulate as the result of its presence in the hydrocarbon reactants and its absorption from the atmosphere. Therefore, alkylation systems employing acid-type catalyst normally include a so-called catalyst "rerun" system through which catalyst is at least periodically passed in order to remove water therefrom. The rerun system will normally involve withdrawing a portion of the catalyst phase as it flows from the separator to the cooler. The withdrawn catalyst phase is heated to a temperature sufficient to vaporize residual alkylate, unreacted hydrocarbons, and the major part of the acid phase from the water. Water is withdrawn as a bottoms product from the rerun separator while the vapor phase is recycled to the settler-surge zone or back to the separated acid phase. Generally, a portion of the alkylatable hydrocarbon, in liquid form, is utilized as a reflux and another portion, in gaseous form, as a stripping medium in the rerun separator.

It is also recognized in the art that a certain amount of dilution of the catalyst phase occurs in the reaction zone itself. Specifically, what is known as a catalyst- or acid-soluble oil (ASO) is produced in the reaction zone, which inherently acts as a diluent for the catalyst phase. While the specific nature of the acid-soluble oil has not been completely established, it is generally accepted that it comprises predominantly polymeric materials with minor amounts of complexes and small or trace amounts of impurities, such as sulfur, to the extent such impurities exist in the alkylation feed materials. These catalyst-soluble oils are retained in the catalyst phase during the separation of the alkylate phase from the catalyst phase and consequently are recycled to the alkylation system. It has also been universally accepted, by those skilled in the art, that the production of catalyst-soluble oil is substantially in excess of that necessary or desirable for dilution of the catalyst. Consequently, the prior art contains suggestions for the removal of the excess catalyst-soluble oil.

Finally, those skilled in the art have recognized the fact that under normal operating conditions the production of catalyst-soluble oils is extremely slow. Accordingly, the prior art has suggested various start-up procedures which will rapidly produce the desirable inventory of catalyst-soluble oil, thereby substantially shortening the time necessary to arrive at full-scale production of alkylate product.

In contrast to the teachings of the prior art, it has now been found that the amount of catalyst diluent which will produce an alkylate product of maximum octane number is within a relatively narrow range below the amounts heretofore suggested by the prior art. Further, it has been found that a very small change in the amount of catalyst diluent, within the narrow range referred to above, has a substantial effect on the octane number of the alkylate product. Also contrary to the teachings of the prior art, it has been found that not all hydrocarbon reactants produce catalyst-soluble oil at the same rate or in the same ultimate volumes. Specifically, it has been found that when reacting an alkylatable hydrocarbon, such as isobutane, with a $C_4$ olefinic hydrocarbon, such as butylene, butene-1 and/or butene-2's, catalyst-soluble oils are produced at an extremely slow rate and in relatively small amounts, as compared with other reaction systems. In addition, as the alkylation reaction proceeds, there is a certain attrition of the amount of catalyst-soluble oils in the catalyst phase. While the reasons for this attrition are not fully known, it is believed that a certain amount of the catalyst-soluble oil is carried over with the alkylate product during separation, a greater portion is removed from the system along with water when the catalyst is rerun to remove water and small amounts may actually be consumed during the alkylation reaction. More specifically, it has been found that when an isoparaffin, such as isobutane, is reacted with a $C_4$ olefinic hydrocarbon, such as butylene, butene-1, and/or butene-2's, an inordinately long period of time is necessary for starting up the alkylation system and there is normally a net loss of catalyst-soluble oil during the course of the reaction. On the other hand, monoolefins, such as $C_3$ and $C_5$ and higher molecular weight hydrocarbons, and diolefins, such as pentadiene and butadiene, produce catalyst-soluble oil in larger amounts and more rapidly.

It would therefore be highly desirable to provide means for substantially shortening the necessary start-up period and for thereafter maintaining a predetermined amount of catalyst-soluble oil in the catalyst system.

It is therefore an object of the present invention to provide an improved system for the alkylation of hydrocarbons. Another and further object of the present invention is to provide an improved system for the alkylation of hydrocarbons, utilizing a cyclic flow of an acid-type catalyst. A further object of the pesent invention is to provide an improved system for the alkylation of hydrocarbons, utilizing a cyclic flow of an acid-type catalyst, in which an alkylate product of improved octane number is obtained. Yet another object of the present invention is to provide an improved system or the alkylation of hydrocarbons, utilizing a cyclic flow of an acid-type catalyst, in which the acid-soluble oil content of the catalyst phase is mantained within a predetermined critical range. Another and further object of the present invention is to provide an improved system for the start-up of a system for the alkylation of hydrocarbons, utilizing cyclic flow of an acid-type catalyst. These and other objects and advantages of the present invention will be apparent from the following detailed description of the

SUMMARY OF THE INVENTION

In accordance with the present invention a method for starting up an integrated process for the simultaneous alkylation of a first alkylatable hydrocarbon comprising an isoparaffinic hydrocarbon with an alkylating agent comprising at least one $C_4$ olefinic hydrocarbon and a second alkylatable hydrocarbon comprising an isoparaffinic hydrocarbon with a second alkylating agent comprising at least one olefinic hydrocarbon selected from the group consisting of $C_3$, $C_5$ and higher hydrocarbons and mixtures thereof is provided, comprising: circulating a first stream of an acid-type catalyst through each of a first reaction zone, a first reaction effluent separation zone and back to said first reaction zone, circulating a second stream of an acid-type catalyst through a second reaction zone, a second reaction effluent separation zone and back to the second reaction zone, contacting an acid-soluble oil precursor selected from the group consisting of $C_3$, $C_5$ and higher olefinic hydrocarbons, a diolefinic hydrocarbon and mixtures thereof with each of said first and said second streams of catalyst until a predetermined amount of acid-soluble oil is present in each of said first and said second streams of catalyst. Once the predetermined concentration of acid-soluble oil has been established in the circulating acid phases such predetermined concentration of acid-soluble oil is maintained by at least periodically adding a portion of one of the first acid phase and the second acid phase or both of said acid phases to the other of the first acid phase and the second acid phase.

Inasmuch as there is some confusion of terminology in the art as to which of the reactants is the alkylatable hydrocarbon and which is the alkylating agent, the isoparaffinic hydrocarbon when referred to herein will be referred to as the alkylatable hydrocarbon while the olefinic hydrocarbon will be referred to as the alkylating agent. Also, the term "catalyst-soluble oil" or "acid-soluble oil" when referred to herein will refer to organic materials derived from the alkylating agent and will exclude unreacted feed hydrocarbons dissolved in the catalyst or acid phase.

DETAILED DESCRIPTION OF THE INVENTION

While, as previously indicated, the present invention can be carried out in any type of reactor system utilizing a cyclically flowing, acid-type catalyst, the preferred system in accordance with the present invention is a cyclic catalyst system in which the mixture of hydrocarbon feed materials is maintained in a liquid state. Such a system is described in detail in U.S. Pat. No. 3,213,157, which is incorporated herein by reference. Briefly, the system comprises a vertically-disposed tubular reactor into which a mixture of the hydrocarbon feed materials and the catalyst is introduced adjacent to the bottom of the reactor, a horizontally-disposed settler-surge vessel, adapted to receive effluent from the top of the reactor and separate the effluent into an alkylate product phase, which is further processed by fractionation or the like, and a catalyst phase, a vertically-disposed tubular catalyst return conduit wherein the catalyst phase passes downwardly, and an essentially horizontally-disposed acid phase cooler, which is cooled by water. This entire system is in open communication throughout for cyclic catalyst flow. Normally, acid phase is at least periodically withdrawn as a side stream from the separated acid phase conduit and passed to a heater where it is heated to a temperature sufficient to cause separation of a liquid phase, comprising predominantly water and some acid-soluble material, and a vapor phase comprising predominantly catalyst, unreacted feed materials and some alkylate. The heated acid phase is then passed to a rerun separator, which is normally operated with a liquid portion of the alkylatable hydrocarbon, as a reflux, and a vapor portion, as a stripping agent. The vapor phase product of the rerun separator is then returned to the systems settler-surge vessel or back to the catalyst phase at a point below or downstream from the point at which catalyst phase was withdrawn for rerun, while the water and any acid-soluble material present is withdrawn as a liquid phase and discarded, or further processed.

Conventionally, the alkylation reaction can comprise the reaction of an isoparaffin with an olefin or other alkylating agent, reaction of a normal paraffin with an olefin or other alkylating agent or the reaction of an aromatic hydrocarbon with an olefin or other alkylating agent. However, as previously indicated, it has been found that the reaction of an isoparaffin with a $C_4$ olefin, such as butylene, butene-1 and/or butene-2's, is peculiar and therefore a preferred embodiment of present invention is directed to a reaction involving these specified materials and mixtures thereof. One preferred mixture is an isoparaffin and a typical mixed "butenes" product from a catalytic cracking operation, which will comprise about 25.0% by volume of butene-1, about 30.0% by volume of isobutylene and about 45.0% by volume of butene-2's. The second reaction involves the utilization of olefin feeds containing significant amounts of $C_3$, $C_5$ and higher hydrocarbons and mixtures thereof.

A variety of alkylation catalysts can be employed in the alkylation reaction, including well known acid catalysts such as sulfuric acid, hydrofluoric acid, phosphoric acid; metal halides, such as aluminum chloride, aluminum bromide, etc.; and other alkylation catalysts. A preferred catalyst for use in the present invention is hydrofluoric acid.

The reaction may be carried out at pressures varying from atmospheric to as high as 1000 psi and higher, preferably about 125 to 220 psia, and at catalyst to total hydrocarbon volume ratios from about 0.1 to about 20. The pressure is preferably sufficient to maintain the hydrocarbon reactants in their liquid phase.

In an alkylation reaction, involving the alkylation of isoparaffins with olefins, a substantial molar excess of isoparaffin to olefin is employed to provide a feed ratio in excess of 1/1, usually about 4/1 to about 70/1 and preferably about 5/1 to about 20/1.

As previously indicated, the reaction zone is preferably maintained under sufficient pressure to insure that the hydrocarbon reactants and the alkylation catalyst are in a liquid phase. The temperature of the reaction will vary with the reactants and with the catalyst employed but generally ranges from between about $-40°$ F. to about 150° F. However, in the reaction of an isoparaffin, such as isobutane, with a $C_4$ olefin, such as butylenes, butene-1 and/or butene-2's, the reaction temperature is preferably between about 60° and about 100° F. and, ideally, about 70° to about 90° F.

The preferred amount of acid-soluble oil built up in the acid phase during start-up and maintained during the conduct of the alkylation reactions is between about 0.4 and about 8.0 weight percent of the total acid phase and even more desirably between about 0.5 and about 6 weight percent. The water content of the acid phase should be between about 0.5 and about 5.0 weight percent of the total acid phase, preferably below about 2.0 and, still more desirably, below about 1.5 weight percent. The total acid-soluble oil and water should be between about 0.9 and about 25 weight percent of the total acid phase and preferably between about 0.9 and about 12 weight percent and still more preferably between about 3 and about 6 weight perecent. Finally, the acidity of the acid phase should be maintained between about 70 and about 95 weight percent of the acid phase and preferably between about 85 and about 90 weight percent. The difference between the acid content of the acid phase and the total of the acid-soluble oil and water in the acid phase will generally be a portion of the isoparaffin feed which has been dissolved in the acid phase.

Conventionally, the system is lined out by first introducing a dried isoparaffinic hydrocarbon to the unit and passing it continuously through the alkylation reactor, the settler, and the isoparaffin stripper and then recycling the same to the alkylation reactor in order to dry out the alkylation apparatus before fresh, essentially anhydrous hydrofluoric acid is introduced. Generally, drying of the feed is accomplished by passing the isoparaffin through molecular sieve dryers or other drying means well known in the art. The dried isoparaffin is then continuously charged to the unit until a rate of continuous recycle equal to the rate of recycle during normal operation is attained. After it has been determined that the alkylation apparatus is sufficiently dry and the isoparaffin recycle rate has been established, hydrofluoric acid is charged to the alkylation apparatus and continuously circulated through the reactor, the settler, the cooler and back to the reactor. This circulation continues until the desired normal circulation rate of hydrofluoric acid is attained. Thereafter, the olefinic feed material is mixed with the isoparaffinic feed material and introduced into the reactor and continuous operation is commenced.

Figure 1A:
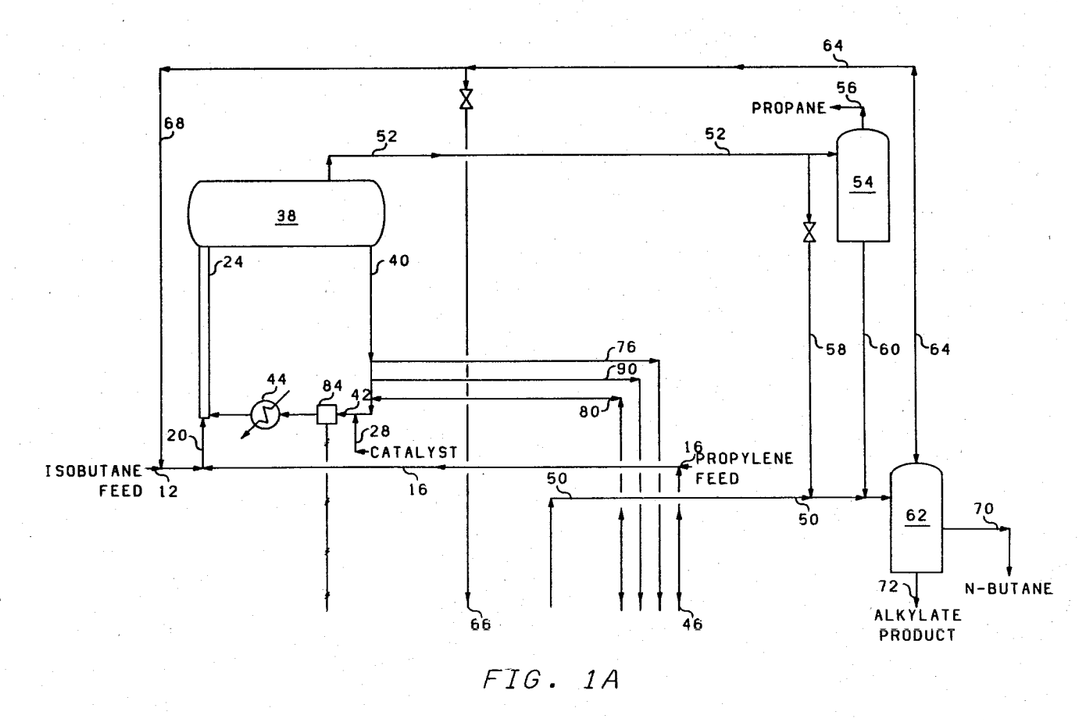
FIGS. 1A and 1B are a simplified flow diagram of an alkylation system in accordance with one embodiment of the present invention.
Figure 1B:
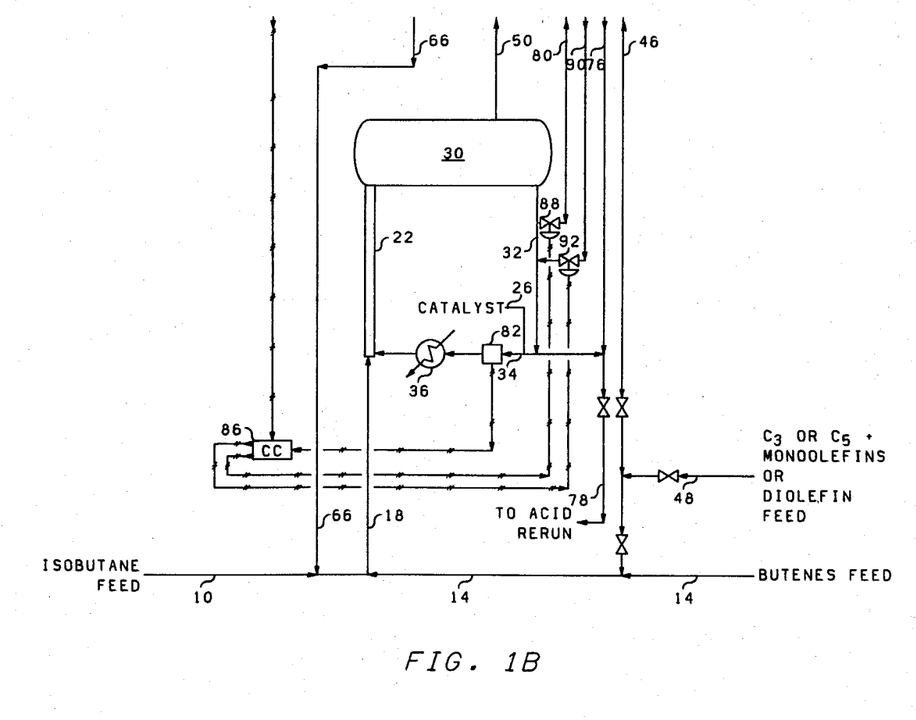

Referring to FIG. 1 of the drawings, the alkylatable hydrocarbon is introduced through lines 10 and 12, respectively. The alkylatable hydrocarbon may be any suitable isoparaffin such as isobutane, isopentane, etc. One or more isohexanes or branched chain heptanes or mixtures thereof may be utilized. However, as illustrated in connection with the drawings, isobutane is the preferred alkylatable hydrocarbon. The alkylating agents are introduced through lines 14 and 16, respectively. The alkylating agents may be any suitable olefinic reactant such as propylene, butene-1, butene-2's, isobutene, the paraffinic and isomeric amylenes, the hexenes, the heptenes or mixtures thereof. In the specific illustration, one alkylating agent stream introduced through line 14 comprises a butenes mixture. Preferably, such a mixture is the product of a catalytic cracking operation and comprises primarily a mixture of isobutene, butene-1 and butene-2's. Such a feed may also be hydroisomerized to convert butene-1 to butene-2's. The other alkylating agent introduced through line 16 is preferably propylene. However, this particular feed material may be selected from the group consisting of $C_3$, $C_5$ and higher olefinic hydrocarbons or mixtures thereof. Either olefinic feed may contain small amounts of diolefins. In the specific embodiment shown, the butenes feed or the butenes and isobutane feed are combined and passed through line 18. The propylene feed and the isobutane feed from line 12 are combined and passed through line 20. From line 18 the reactants pass upwardly through a vertically disposed tube-type reactor 22 while the feeds from lines 12 and 16 and line 20 pass upwardly through tube-type reactor 24. Acid-type catalyst, in the preferred embodiment hydrofluoric catalyst, is introduced to reactor 22 through line 26 while hydrofluoric catalyst is introduced to reactor 24 through line 28. Lines 26 and 28 also serve for the introduction of make-up catalyst and the recycle of separated purified rerun catalyst during continuous operation of the alkylation systems. The feed materials and acid, after reaction in reactor 22, pass to a first separator 30 which is actually a settler-surge vessel which serves to separate the reactor effluent stream into an acid phase which is discharged through vertically disposed line 32 thence to line 34 and finally through cooler 36 to reactor 22. Cooler 36, in the specific embodiment described, is actually a horizontally-disposed, elongated cooler wherein acid is introduced into one end while the reactants are introduced into the other end adjacent the bottom of the reactor. Similarly, an effluent stream from reactor 24 passes to the second settler-surge vessel 38 which separates the effluent into an alkylate phase and an acid phase and the acid phase is discharged downwardly through line 40 to line 42. From line 42 the acid phase passes through cooler 44 back to reactor 24.

As previously indicated, the systems are normally lined out by circulating the alkylatable hydrocarbon through the unit under reaction conditions until the desired circulation rate is attained, the acid is then similarly circulated through the systems until the desired acid rate is attained and, finally, the alkylating agent is introduced to the reactors alone or in admixture with the alkylatable hydrocarbon. However, in accordance with the present invention, this common procedure needs to be varied for reasons which will be apparent since, as previously indicated, $C_4$ olefinic hydrocarbons generate acid-soluble oil very slowly and in small amounts and in accordance with the present invention the normal $C_4$ olefin feed is not utilized in startup of the system. Instead, a monoolefin $C_3$, $C_5$ and higher or diolefin feed or mixtures thereof is utilized. Obviously, where propylene is utilized as a feed in the companion unit, a portion of the propylene feed may be passed downwardly through line 46 thence through a continuation of line 14 and line 18 to reactor 22. At the same time, propylene feed will be passed through line 16 and line 20 to reactor 24. Alternatively, $C_5$ and higher monoolefins or a diolefin from an outside source may be introduced through line 48. Irrespective of the procedure for lining out the systems, acid must be circulating through cooler 44, reactor 24, separator 38, line 40 and line 42 as well as through line 26, cooler 36, reactor 22, separator 30 and lines 32 and 34 so that the acid is circulating through the primary reaction systems at its usual rate and at reaction conditions in reactors 22 and 24. Whether the olefin or diolefin materials are introduced and circulated before or after acid circulation is established is immaterial so long as the acid and olefinic hydrocarbons are present in the reactors 22 and 24 under reaction conditions. This is so since the desired procedure is to first build up a predetermined quantity of acid-soluble oil in the circulating acid phases and this generation of acid-soluble oil is preferably carried out before introduction of the alkylatable hydrocarbon to either of the reaction systems. Once the predetermined amount of acid-soluble oil has been built up in both streams of circulating acid phase, flow of feed materials is switched to the desired alkylating agents, if these have not been employed in generating acid-soluble oil during startup, and flow of the alkylatable hydrocarbon is begun. Accordingly, a continuous reaction should therefore be taking place at this point and, due to the improved start-up procedure, in a substantially shortened period of time. Under normal reaction conditions and with the appropriate feed materials, an alkylate product separated in separator 30 will be withdrawn through line 50 while the alkylate product from separator 38 will be withdrawn through line 52. Where the alkylating agent in reactor 24 is propylene, the alkylate from line 52 is passed to the depropanizer 54 where propane formed or present in the feed is withdrawn through line 56. To the extent that little or no propane is present in the alkylate phase in line 52, all or part of the alkylate phase may be passed through line 58. The depropanized alkylate phase from unit 54 is passed through line 60. The depropanized alkylate phase or all or part of the alkylate phase from line 52 then mixes with the alkylate product from separator 30 passing through line 50. The combined alkylate phases are then passed through alkylatable hydrocarbon stripper or isostripper 62. Stripper 62 is adapted to separate from the alkylate phases excess alkylatable hydrocarbon which is discharged through line 64 and then is recycled to reactor 22 through line 66 and/or to reactor 24 through line 68. A paraffin fraction such as vaporous normal butane may be withdrawn as a side stream from stripper 62 through line 70. The final liquid alkylate product is discharged as a bottoms product from stripper 62 through line 72. Obviously, other numbers and arrangements of fractionators or separators may be utilized depending upon the character of the reactor effluents.

During the normal operation of the alkylation systems, excess water will accumulate in the acid phase due to the presence of water in the feed materials and/or absorption of water from the atmosphere. Consequently, at least periodically, the acid phase is withdrawn through lines 74 and 76, respectively, and are then passed through line 78 to an acid rerun system (not shown). In the acid rerun system water is removed from the acid phase and the acid is purified and returned to the system as a makeup or rerun acid through lines 26 and 28. In the rerun system a certain amount of the acid-soluble oils will be removed along with the water. Consequently, one or both of the reaction systems must be supplied with additional acid-soluble oil. If both units are deficient in acid-soluble oil then the deficiency may be made up by adding additional olefin or diolefin through line 48, as previously indicated in connection with startup of the system. However, normally there will be an excess of acid-soluble oil in the system circulating the acid phase through reactor 24 and a deficiency in the system including reactor 22. Therefore, in accordance with one embodiment of the present invention the acid-soluble oil in the acid phases is balanced by passing a portion of the acid-soluble oil from the system including reactor 22 to the system including reactor 24 through line 80. In order to effect this balance the volume of acid-soluble oil in the system including reactor 22 is measured by detector 82 and that in the system including reactor 24 is measured by detector 84. The two detectors send a signal to the appropriate computer controller 86. Controller 86 will in turn transmit a signal to flow valve 88. Flow valve 88 in this instance would be mounted in line 80 and would be a two-way valve adapted to pass acid-soluble oil from the system including reactor 22 to the system including 24 or in the reverse direction depending upon the signal from controller 86. A small reversible pump or preferably an isoparaffin-powered eductor (not shown) can also be used to transfer the catalyst through conduit 80 in one or the other directions. However, in another embodiment an additional line 90 would connect conduits 32 and 40 thus permitting flow of acid phase from the system including reactor 24 to the system including reactor 22. Accordingly, in this embodiment, transmission of acid phase between the two systems would go in one direction through line 80 and in the opposite direction through line 90. For this purpose, a valve 92 would be mounted in line 90 and both valves 88 and 92 would be controlled by an appropriate controller such as 86. Normally, the transfer of acid-soluble oil in the catalyst phase will be passed via line 90 from conduit 40 of the propylene alkylation to conduit 32 of the butylenes alkylation.

Figure 2A:
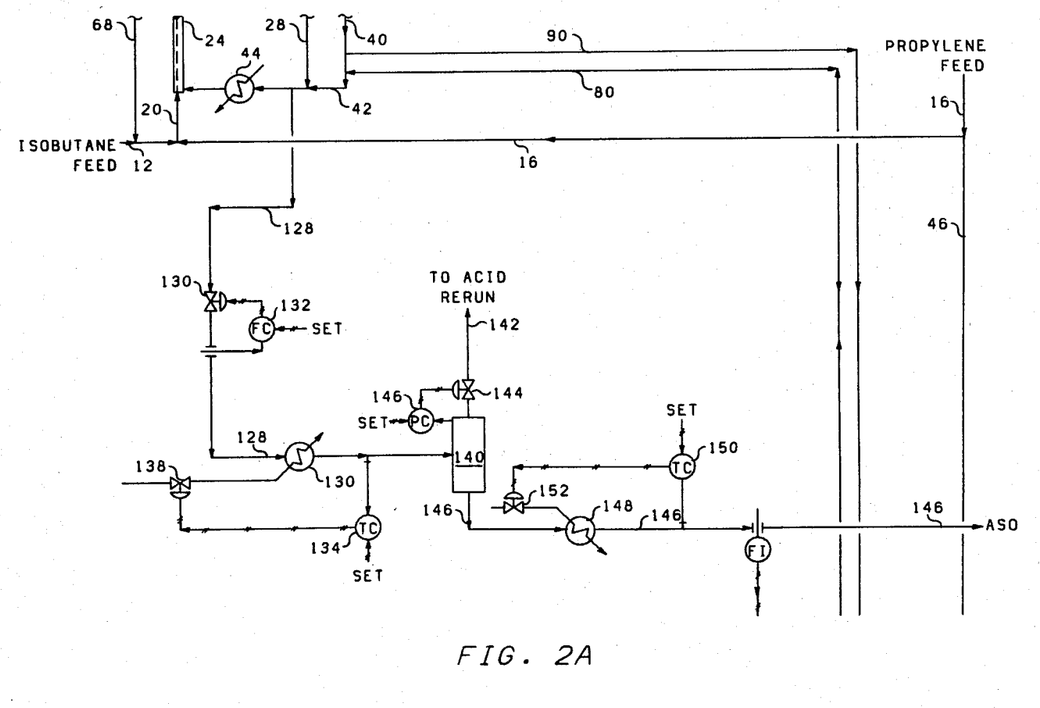
FIGS. 2A and 2B a more detailed diagram of a control means for the system of FIGS. 1A and 1B.
Figure 2B:
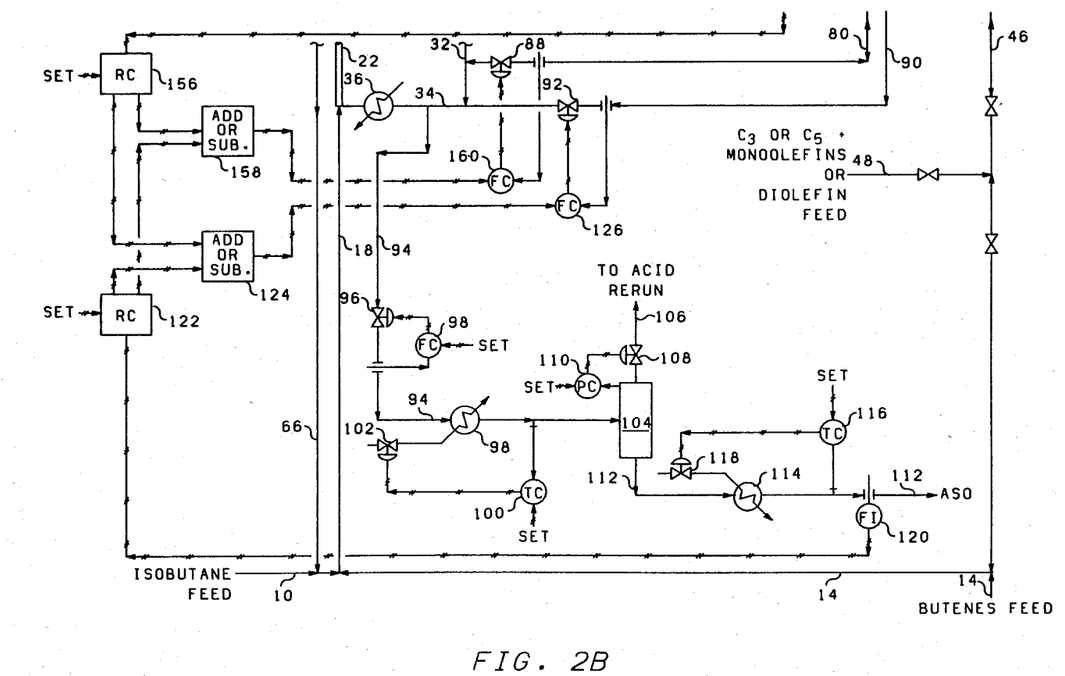

FIG. 2 of the drawings illustrates in more detail an appropriate control system 82-86-92 and 84-86-88. In accordance with FIG. 2 a slip stream of acid phase is removed from the recycle acid phase stream, preferably after any rerun or recycle acid is introduced through line 32 and before cooling. This slip stream of acid phase is withdrawn through line 94. The amount of acid phase withdrawn through line 94 is controlled by valve 96 which in turn is controlled by flow controller 98. The sample in line 94 is heated by means of heating means 98. The temperature to which the sample of acid phase is heated is controlled by means of temperature controller 100 which in turn controls valve 102 in the line supplying heating medium to heating means 98. The sample is increased in temperature to a temperature sufficient to vaporize acid isoparaffin and water and is passed to separator 104. From separator 104 the vapors are discharged through line 106, controlled by valve 107 which in turn is controlled by pressure controller 110. The vapors can if desired be passed to the acid rerun system (not shown). However, since the sample withdrawn through line 94 is so small, this small volume of acid can be discarded if desired. The acid soluble oil removed from the acid phase sample is withdrawn through line 112 and its temperature is reduced in cooling means 114. Cooling means 114 is controlled by temperature controller 116 which in turn controls valve 118 in the line supplying cooling medium to cooler 114. Again, since the sample of acid phase withdrawn through line 94 is extremely small, the withdrawal of this sample will in no way alter the operation of the alkylation system and it is normally sufficiently small that it can be disposed of without any measurable effect on the cost of operation. The amount of separated acid-soluble oil is measured by flow indicator 120 which sends a signal to ratio controller 122 which in turn sends a signal to add or subtract circuit 124. Add or subtract circuit 124 controls flow controller 126 which in turn controls valve 92.

The control system for the alkylation system including reactor 24 is substantially the same as that for the system including reactor 22. More specifically, a small slip stream of system catalyst is withdrawn through line 128. The volume of the acid phase sample withdrawn through line 128 is controlled by valve 130 and flow controller 132. The acid phase sample in line 128 is heated by heating means 130 and its temperature controlled by means of temperature controller 134 and valve 138 in the line passing heating medium through heater 130. The heated sample is then passed to separator 140. In separator 140 acid in a vapor state including, isoparaffin and water is discharged through line 142 and may be returned to the acid rerun unit (not shown). The pressure in separator 140 is controlled by means of valve 144 in line 142 and pressure controller 146. The separated acid-soluble oil is withdrawn from separator 140 through line 146. The withdrawn acid-soluble oil is cooled by cooling means 148 whose temperature is controlled by temperature controller 150 which in turn controls valve 152 in the line supplying cooling medium to cooler 148. As in the previous instance, the acid-soluble oil from the sample of the acid phase may be discarded without in any way upsetting the system or adding to the cost of operation. The amount of acid-soluble oil in line 146 is measured by flow indicator 154. Flow indicator 154 sends a signal to ratio controller 156 which in turn sends a signal to add or subtract circuit 158. The signal from add or subtract circuit 158 is sent to flow controller 160 which in turn controls valve 88. As is appropriate where the flow through lines 80 and 90 are both being controlled ratio controllers 122 and 156 are interconnected with add and subtract circuits 124 and 158. As previously indicated, it would be obvious to one skilled in the art that a single line connecting acid phase discharge lines 32 and 40 can be utilized, in which case a single sampling analyzing and flow control would be utilized and the elements thereof would, of course, be obvious to one skilled in the art from the prior description. It will also be obvious to one skilled in the art that either or both of the control systems may be utilized for detecting the amount of acid-soluble oil in recycled acid phases and terminating the flow of acid-soluble oil to the recycle systems when the predetermined amount of acid-soluble oil in each recycle acid phase has reached its predetermined amount.

Figure 3A:
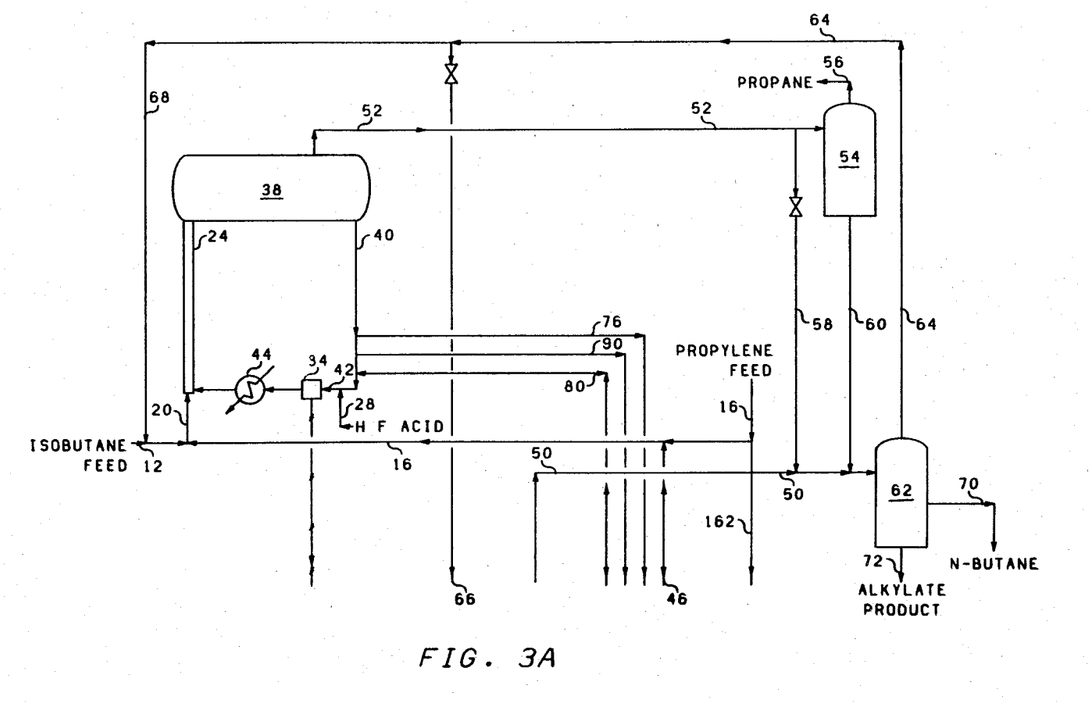
FIGS. 3A and 3B are a simplified flow diagram of a second embodiment of the present invention.
Figure 3B:
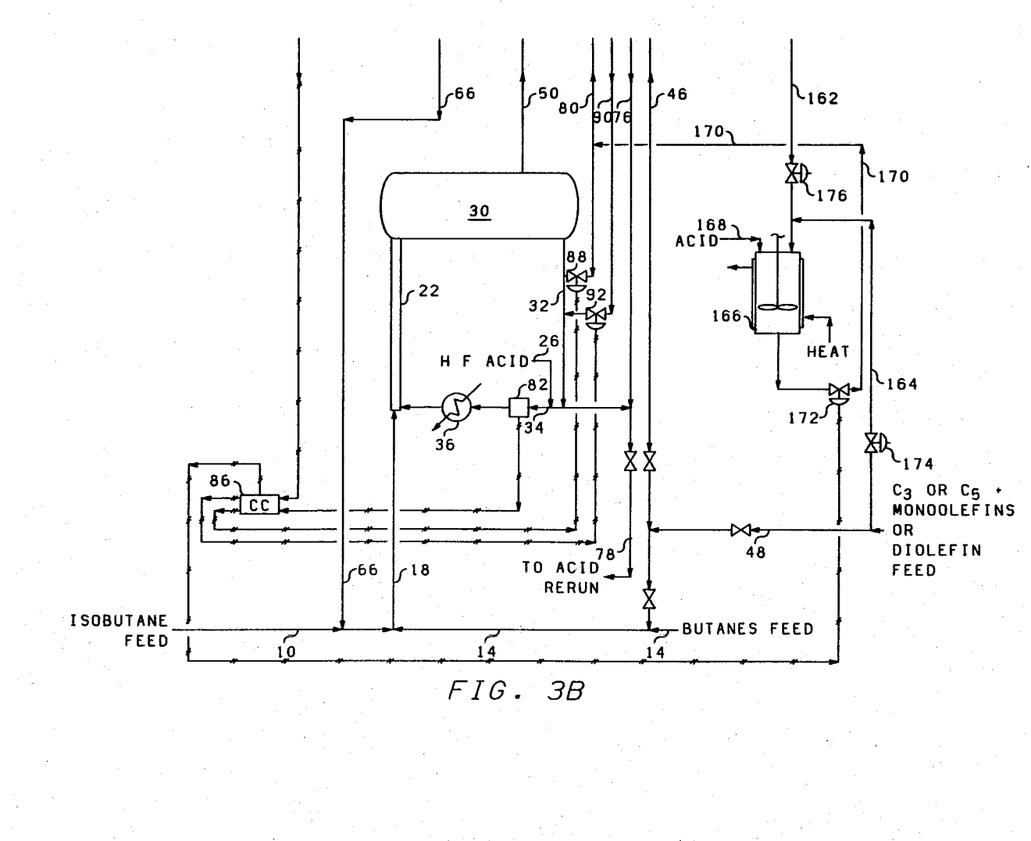

FIG. 3 illustrates another embodiment of the present invention including alternate means for producing additional acid-soluble oil, as needed. The system of FIG. 3 is substantially the same as that of FIG. 1, except that the system of FIG. 3 incorporates a heating means for heating acid-soluble oil precursors to a temperature higher than the alkylation reaction temperature in order to form acid-soluble oil in larger quantities and/or at a more rapid rate. While, in the specific alternative shown, the heating means is an acid-soluble oil reactor, a simple heater may be substituted therefor. In accordance with FIG. 3, propylene, $C_5+$ monoolefins or diolefins from an outside source may be introduced through lines 162 and 164, respectively, to a stirred and heated reactor 166. Reactor 166 would be supplied with fresh or rerun acid from line 26 or 28 or with acid phase from line 32 or 40 through line 168. By utilizing a reactor, such as 166, the generation of acid-soluble oil can be carried out at temperatures, pressures and contact times more conducive to the formation of acid-soluble oil than the alkylation system conditions. Where unit 166 is a heater, no acid would be supplied. The generated acid-soluble oil or the heated olefinic material would be introduced to the reaction systems through line 170. In the latter case, the heated olefinic material would react with the acid phase in lines 32 and/or 40 and generate acid-soluble oil in situ. Acid-soluble oil or heated olefinic material addition could be controlled by control valve 172 in line 170, as dictated by computer-controller 86. It is also obvious that computer-controller 86 could be appropriately modified and connected to valves 174 and 176 in lines 164 and 162, respectively. Another obvious alternative would be to feed acid-soluble oil or heated olefinic material from line 170 to both lines 80 and 90, as necessary. It is further obvious that this alternative system can be utilized either during startup or to at least periodically add acid-soluble oil during the course of the alkylation reactions.

Figure 4:
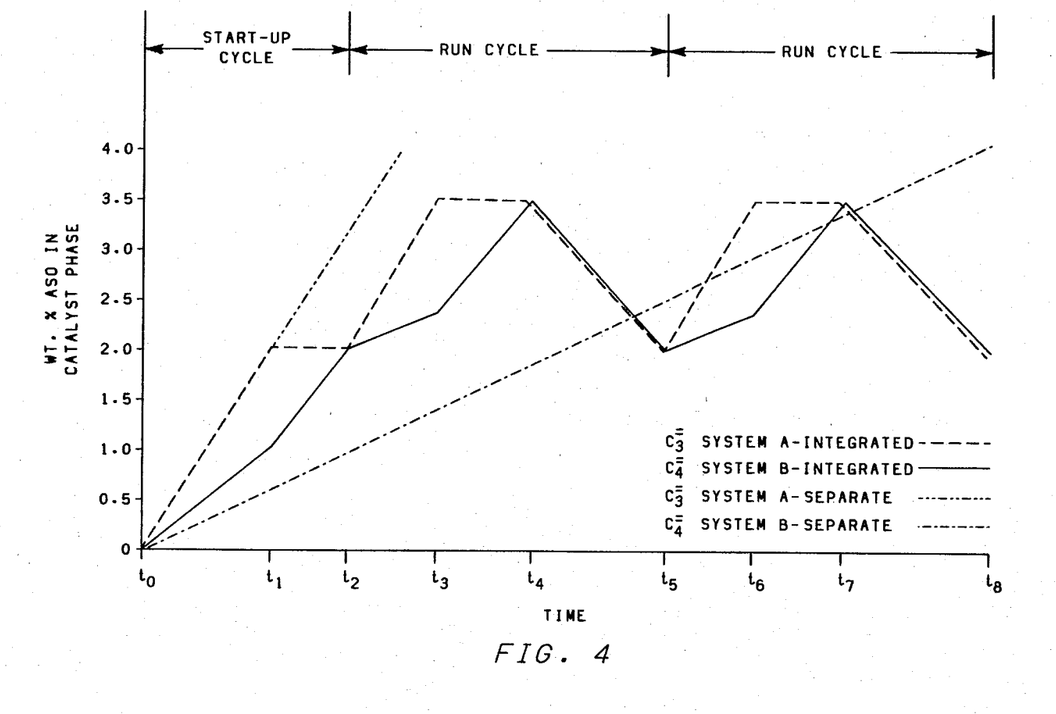
FIG. 4 is a plot illustrating the acid-soluble oil content of the catalyst phase versus time when operating in accordance with the prior art and when operating in accordance with the present invention.

An exemplary mode of operation, in accordance with the present invention is illustrated in FIG. 4. FIG. 4 is a plot of time versus acid-soluble oil content in the acid phases for an integrated process in which isobutane is alkylated with propylene at 120° F. in one reactor and isobutane is alkylated with butenes at 90° F. in a second reactor. In this example, the acid-soluble oil content is adjusted between a minimum of 2.0 weight percent and a maximum of 3.5 weight percent to attain and maintain an optimum value of about 2.75 weight percent. The dash-double-dot line represents an operation in which isobutane is alkylated with propylene (designated System A) as a separate and distinct operation. The dash-dot line represents an operation in which isobutane is alkylated with butenes (designated System B) as a separate and distinct operation. The dashed line represents the operation of System A as part of the integrated system of the present invention. The solid line represents the operation of System B as part of the integrated system of the present invention. During the time period $t_0$ to $t_1$, the integrated system is operated by adding propylene to the butenes feed in System B until the acid-soluble oil content in the acid phase of System A reaches 2.0 weight percent. From $t_1$ to $t_2$, the acid-soluble oil content in System A is held at 2.0 weight percent by continuing the addition of propylene to System B and transferring acid phase from System A to System B and acid phase from System B to System A in equal amounts. At time $t_2$, the start-up cycle has been completed and normal operation can begin. During the period $t_2$ to $t_3$, the addition of propylene to System B and the interchange of acid phase between System A and System B are discontinued until the acid-soluble oil content of the acid phase of System A reaches 3.5 weight percent. From $t_3$ to $t_4$, equal amounts of acid-soluble oil are interchanged between System A and System B, thereby holding the acid-soluble oil content of the acid-phase of System A at 3.5 weight percent until the acid-soluble oil content of System B reaches 3.5 weight percent. The acid phases of both System A and System B are then rerun for the period $t_4$ to $t_5$. During the rerun period acid-soluble oil is being removed from the two acid phases along with water. The acid phase reruns are continued until the acid-soluble oil contents of the acid phases of both Systems A and B drop to 2.0 weight percent. The temperature of both systems are also adjusted appropriately during this period. As shown by the periods $t_5$ to $t_6$, $t_6$ to $t_7$ and $t_7$ to $t_8$, the operations during periods $t_2$ to $t_3$, $t_3$ to $t_4$ and $t_4$ to $t_5$, respectively, are then repeated. The advantages of the present integrated system, both during startup and normal operation are quite obvious from FIG. 4.

While specific materials, conditions and equipment have been referred to herein by way of example, it is to be understood that numerous variations and equivalents thereof will be apparent to one skilled in the art and such examples are not to be construed as limitations.

I claim:

1. Apparatus for alkylating at least one alkylatable hydrocarbon with two different alkylating agents in the presence of an acid-type catalyst comprising:
   (a) a first alkylation reactor system, including;
      (1) a first alkylation reactor means;
      (2) alkylatable hydrocarbon introduction means adapted to introduce an alkylatable hydrocarbon into said first reactor;
      (3) first alkylating agent introduction means adapted to introduce a first alkylating agent into said first reactor;
      (4) first separator means operatively connected to the effluent end of said first reactor and adapted to separate said effluent into a first alkylate phase and a first acid phase; and
      (5) first catalyst recycle means operatively connected to said first separator to receive said first acid phase and pass said first acid phase from said first separator to said first reactor;
   (b) a second alkylation reactor system, including;
      (1) second alkylation reactor means;
      (2) alkylatable hydrocarbon introduction means adapted to introduce an alkylatable hydrocarbon into said second reactor;
      (3) second alkylating agent introduction means separate from said first alylating agent introduction means and adapted to introduce a second alkylating agent into said second reactor;
      (4) second separator means operatively connected to the effluent end of said second reactor and adapted to separate said effluent into a second alkylate phase and a second acid phase; and
      (5) second catalyst recycle means operatively connected to said second separator means to receive said second acid phase and pass said second acid phase from said second separator means to said second reactor means;
   (c) at least one catalyst exchange means operatively connecting said first catalyst recycle means and said second catalyst recycle means;
   (d) acid soluble oil generation means operatively connected to at least one of said first catalyst recycle means, said second catalyst recycle means and said catalyst exchange means;
   (e) said acid soluble oil generation means, includes; a third alkylating agent introduction means, operatively connected to said acid soluble oil generation means and a source of alkylating agent, olefinic hydrocarbon introduction means, operatively connected to said acid soluble oil generation means and a source of at least one olefinic hydrocarbon, other than said first and second alkylating agents, and acid-type catalyst introduction means, operatively connected to said acid soluble oil generation means and a source of supply of acid-type catalyst, said third alkylating agent introduction means, said olefinic hydrocarbon introduction means and said acid-type catalyst introduction means being the only means for introducing reactants to said acid soluble oil generation means;

(f) heating means operatively connected to said acid-soluble oil generation means; and (g) control means to alternatively (1) open said third alkylating agent introduction means, close said olefinic hydrocarbon introduction means and actuate and increase the heat output of said heating means to a temperature significantly above the temperature of said first acid phase, said second acid phase or the acid present in said catalyst exchange means, to thereby produce acid soluble oil at a rate greater than that produced in said first and second alkylation reactor means, and (2) open said olefinic hydrocarbon introduction means, close said third alkylating agent introduction means and actuate and increase the heat output of said heating means to a temperature sufficient to produce acid soluble oil in greater quantities than that produced in said first and second alkylation reactor means.

2. Apparatus in accordance with claim 1 which additionally includes control means operatively connected to the first catalyst recycle means, the second catalyst recycle means and the catalyst exchange means and adapted to maintain predetermined amounts of acid-soluble oil in at least one of the first acid phase and the second acid phase.

3. Apparatus in accordance with claim 1 wherein the source of the third alkylating agent thus connected to the acid soluble oil generator is at least one of the source of the first alkylating agent and the source of the second alkylating agent.

4. Apparatus in accordance with claim 1 wherein the source of the acid-type catalyst thus connected to the acid soluble oil generator is at least one of fresh acid-type catalyst, re-run acid-type catalyst, a portion of the first acid phase, a portion of the second acid phase and at least a portion of the acid phase present in the catalyst exchange means.

5. Apparatus for alkylating at least one alkylatable hydrocarbon with two different alkylating agents in the presence of an acid-type catalyst comprising:

(a) a first alkylation reactor system, including;
  (1) first alkylation reactor means;
  (2) alkylatable hydrocarbon introduction means adapted to introduce an alkylatable hydrocarbon into said first reactor;
  (3) first alkylating agent introduction means adapted to introduce a first alkylating agent into said first reactor;
  (4) first separator means operatively connected to the effluent end of said first reactor and adapted to separate said effluent into a first alkylate phase and a first acid phase; and
  (5) first catalyst recycle means operatively connected to said first separator to receive said first acid phase and pass said first acid phase from said first separator to said first reactor;

(b) a second alkylation reactor system, including;
  (1) second alkylation reactor means;
  (2) alkylatable hydrocarbon introduction means adapted to introduce an alkylatable hydrocarbon into said second reactor;
  (3) second alkylating agent introduction means separate from said first alkylating agent introduction means and adapted to introduce a second alkylating agent into said second reactor;
  (4) second separator means operatively connected to the effluent end of said second reactor and adapted to separate said effluent into a second alkylate phase and a second acid phase; and
  (5) second catalyst recycle means operatively connected to said second separator means to receive said second acid phase and pass said second acid phase from said second separator means to said second reactor means;

(c) at least one catalyst exchange means operatively connecting said first catalyst recycle means and said second catalyst recycle means;

(d) acid soluble oil generation means operatively connected to at least one of said first catalyst recycle means, said second catalyst recycle means and said catalyst exchange means and adapted to generate acid-soluble oil at at least one of a more rapid rate and in greater quantities than that generated in either of said first reactor means or said second reactor means;

(e) third alkylating agent introduction means adapted to introduce additional alkylating agent, in excess of said first alkylating agent to said first reactor and said second alkylating agent to said second reactor, to said acid-soluble oil generating means;

(f) heating means operatively connected to said acid-soluble oil generating means and adapted to heat said third alkylating agent to a temperature significantly above the temperature of said first acid phase, said second acid phase or the acid phase present in said catalyst exchange means; and (g) control means operatively connected to said first catalyst recycle means, said second catalyst recycle means and said catalyst exchange means and adapted to maintain predetermined amounts of acid-soluble oil in at least one of said first acid phase and said second acid phase, including;
  (1) acid-soluble oil measuring means operatively connected to at least one of said first catalyst recycle means and said second catalyst recycle means and adapted to sample at least one of said first acid phase and said second acid phase and measure the amount of acid-soluble oil therein; and
  (2) acid-soluble oil adjusting means operatively connected to said measuring means and at least one of said catalyst exchange means and said acid-soluble oil generating means and adapted to maintain said predetermined amounts of acid-soluble oil in said first acid phase and said second acid phase by at least one of transferring acid phase between said first catalyst recycle means and said second catalyst recycle means and adding acid-soluble oil from said acid-soluble oil generating means to one of said first catalyst recycle means and said second catalyst recycle means in response to the thus measured amount of acid-soluble oil in said first acid phase and said second acid phase, respectively.

6. Apparatus in accordance with claim 5 wherein the measuring means includes volume measuring means adapted to measure the volume of the thus separated liquid acid-soluble oil.

7. Apparatus in accordance with claim 5 wherein the measuring means includes separating means adapted to separate the acid-soluble oil of the thus sampled acid phase, as a liquid phase, from the remaining components of the thus sampled acid phase, as a vapor phase.

8. Apparatus in accordance with claim 7 wherein the separating means includes heating means adapted to vaporize the remaining components of the thus sampled acid phase while leaving unvaporized the acid-soluble oil content of said sampled acid phase.

9. Apparatus in accordance with claim 8 wherein the separating means includes vapor-liquid separator means adapted to thus separate the liquid acid-soluble oil phase from the gaseous remaining components of the thus sampled acid phase.

10. Apparatus for alkylating at least one alkylatable hydrocarbon with two different alkylating agents in the presence of an acid-type catalyst comprising:
   (a) a first alkylation reactor system, including;
      (1) first alkylation reactor means;
      (2) alkylatable hydrocarbon introduction means adapted to introduce an alkylatable hydrocarbon into said first reactor;
      (3) first alkylating agent introduction means adapted to introduce a first alkylating agent into said first reactor;
      (4) first separator means operatively connected to the effluent end of said first reactor and adapted to separate said effluent into a first alkylate phase and a first acid phase; and
      (5) first catalyst recycle means operatively connected to said first separator means to receive said first acid phase and pass said first acid phase from said first separator to said first reactor;
   (b) a second alkylation reactor system, including;
      (1) second alkylation reactor means;
      (2) alkylatable hydrocarbon introduction means adapted to introduce an alkylatable hydrocarbon into said second reactor;
      (3) second alkylating agent introduction means separate from said first alkylating agent introduction means and adapted to introduce a second alkylating agent into said second reactor;
      (4) second separator means operatively connected to the effluent end of said second reactor and adapted to separate said effluent into a second alkylate phase and a second acid phase; and
      (5) second catalyst recycle means operatively connected to said second separator to receive said second acid phase and pass said second acid phase from said second separator means to said second reactor means;
   (c) acid-soluble oil generation means operatively connected to at least one of said first catalyst recycle means and said second catalyst recycle means;
   (d) said acid soluble generation means, includes; a third alkylating agent introduction means, operatively connected to said acid soluble oil generation means and a source of alkylating agent, olefinic hydrocarbon introduction means, operatively connected to said acid soluble oil generation means and a source of at least one olefinic hydrocarbon, other than said first and second alkylating agents, and acid-type catalyst introduction means, operatively connected to said acid soluble oil generation means and a source of supply of acid-type catalyst, said third alkylating agent introduction means, said olefinic hydrocarbon introduction means and said acid-type catalyst introduction means being the only means for introducing reactants to said acid soluble oil generation means;
   (e) heating means operatively connected to said acid-soluble oil generation means; and
   (f) control means to alternatively (1) open said third alkylating agent introduction means, close said olefinic hydrocarbon introduction means and actuate and increase the heat output of said heating means to a temperature significantly above the temperature of said first acid phase or said second acid phase, to thereby produce acid soluble oil at a rate greater than that produced in said first and second alkylation reactor means, and (2) open said olefinic hydrocarbon introduction means, close said third alkylating agent introduction means and actuate and increase the heat output of said heating means to a temperature sufficient to produce acid soluble oil in greater quantities than that produced in said first and second alkylation reactor means.

11. Apparatus in accordance with claim 10 wherein the source of the alkylating agent thus connected to the acid soluble oil generator is at least one of the source of the first alkylating agent and the source of the second alkylating agent.

12. Apparatus in accordance with claim 10 wherein the source of the acid-type catalyst thus connected to the acid soluble oil generator is at least one of fresh acid-type catalyst, re-run acid-type catalyst, a portion of the first acid phase and a portion of the second acid phase.

13. Apparatus for alkylating at least one alkylatable hydrocarbon with two different alkylating agents in the presence of an acid-type catalyst comprising:
   (a) a first alkylation reactor system, including;
      (1) first alkylation reactor means;
      (2) alkylatable hydrocarbon introduction means adapted to introduce an alkylatable hydrocarbon into said first reactor;
      (3) first alkylating agent introduction means adapted to introduce a first alkylating agent into said first reactor;
      (4) first separator means operatively connected to the effluent end of said first reactor and adapted to separate said effluent into a first alkylate phase and a first acid phase; and
      (5) first catalyst recycle means operatively connected to said first separator means to receive said first acid phase and pass said first acid phase from said first separator to said first reactor;
   (b) a second alkylation reactor system, including;
      (1) second alkylation reactor means;
      (2) alkylatable hydrocarbon introduction means adapted to introduce an alkylatable hydrocarbon into said second reactor;
      (3) second alkylating agent introduction means separate from said first alkylatng agent introduction means and adapted to introduce a second alkylating agent into said second reactor;
      (4) second separator means operatively connected to the effluent end of said second reactor and adapted to separate said effluent into a second alkylate phase and a second acid phase; and
      (5) second catalyst recycle means operatively connected to said second separator to receive said second acid phase and pass said second acid phase from said second separator means to said second reactor means;
   (c) acid-soluble oil generation means operatively connected to at least one of said first catalyst recycle means and said second catalyst recycle means and adapted to generate acid-soluble oil at at least one of a more rapid rate and in greater quantities than that generated in either of said reactor or said second reactor.

(d) third alkylating agent introduction means adapted to introduce additional alkylating agent, in excess of that introduced as said first alkylating agent to said first reactor and said second alkylating agent to said second reactor, to said acid-soluble oil generator means;
(e) heating means operatively connected to said acid-soluble oil generating means and adapted to heat said third alkylating agent to a temperature sufficient to thus generate acid-soluble oil; and
(f) control means operatively connected to said first catalyst recycle means and said second catalyst recycle means and adapted to maintain predetermined amounts of acid-soluble oil in at least one of said first acid phase and said second acid phase, including;
  (1) acid-soluble measuring means operatively connected to at least one of the first catalyst recycle means and the second catalyst recycle means and adapted to sample at least one of the first acid phase and the second acid phase and measure the amount of acid-soluble oil therein; and
  (2) acid-soluble oil adjusting means operatively connected to said measuring means and said acid-soluble oil generating means and adapted to maintain the predetermined amounts of acid-soluble oil in said first acid phase and second acid phase by adding acid-soluble oil from said acid-soluble oil generation means to one of said first catalyst recycle means and said second catalyst recycle means in response to the thus measured amount of acid-soluble oil in said first acid phase and said second acid phase, respectively.

14. Apparatus in accordance with claim 13 wherein the measuring means includes volume measuring means adapted to measure the volume of the thus separated liquid acid-soluble oil.

15. Apparatus in accordance with claim 13 wherein the measuring means includes separating means adapted to separate acid-soluble oil of the thus sampled acid phase, as a liquid phase, from the remaining components of the thus sampled acid phase as a vapor phase.

16. Apparatus in accordance with claim 15 wherein the separating means includes heating means adapted to vaporize the remaining components of the thus sampled acid phase while leaving unvaporized the acid-soluble oil content of said sampled acid phase.

17. Apparatus in accordance with claim 16 wherein the separating means includes vapor-liquid separator means adapted to thus separate the liquid acid-soluble oil phase from the gaseous remaining components of the thus sampled acid phase.

* * * * *

UNITED STATES PATENT AND TRADEMARK OFFICE
CERTIFICATE OF CORRECTION

PATENT NO. : 4,500,490
DATED : February 19, 1985
INVENTOR(S) : Thomas Hutson, Jr.

It is certified that error appears in the above-identified patent and that said Letters Patent are hereby corrected as shown below:

Column 12, line 34, Claim 1, delete "alylating" and substitute ---alkylating---

Column 16, line 67, claim 13, after :said" and before "reactor", insert ---first---

Signed and Sealed this

First Day of October 1985

[SEAL]

Attest:

DONALD J. QUIGG

Attesting Officer

Commissioner of Patents and
Trademarks—Designate